US006236876B1

(12) United States Patent
Gruner et al.

(10) Patent No.: US 6,236,876 B1
(45) Date of Patent: May 22, 2001

(54) NAVIGABLE PROBE AND MOTOR CONTROL APPARATUS

(75) Inventors: George Paul Gruner, Mukilteo, WA (US); Marlan James Bell, Beaverton; Guy Louis Letourneau, Warren, both of OR (US)

(73) Assignee: The Whitaker Corporation, Wilmington, DE (US)

( * ) Notice: Subject to any disclaimer, the term of this patent is extended or adjusted under 35 U.S.C. 154(b) by 0 days.

(21) Appl. No.: 08/920,632

(22) Filed: Aug. 29, 1997

Related U.S. Application Data (60) Provisional application No. 60/024,885, filed on Aug. 30, 1996, and provisional application No. 60/051,333, filed on Jun. 30, 1997.

(51) Int. Cl.[7] .................................................. A61B 5/05
(52) U.S. Cl. .......................... 600/407; 600/146; 600/437; 600/459; 600/462; 600/434; 600/444; 600/445; 600/114; 600/149
(58) Field of Search ................................... 600/407, 146, 600/437, 459, 462, 434, 444, 445, 114, 149

(56) References Cited

U.S. PATENT DOCUMENTS

| 4,503,842 | * | 3/1985 | Takayama | 600/146 |
| 4,559,928 | * | 12/1985 | Takayama | 600/146 |
| 4,586,079 | * | 4/1986 | Cooper et al. | 358/100 |
| 4,924,852 | * | 5/1990 | Suzuki et al. | 600/146 |
| 5,158,086 | | 10/1992 | Brown et al. | 128/662.03 |
| 5,445,154 | | 8/1995 | Larson et al. | 128/660.1 |
| 5,482,029 | * | 1/1996 | Sekiguchi et al. | 600/109 |
| 5,634,466 | * | 6/1997 | Gruner | 600/136 |
| 5,769,086 | * | 6/1998 | Ritchart et al. | 600/105 |
| 5,808,665 | * | 9/1998 | Green | 600/101 |
| 5,833,616 | * | 11/1998 | Gruner et al. | 600/462 |
| 5,842,993 | * | 12/1998 | Eichelberger et al. | 600/462 |
| 5,897,504 | * | 4/1999 | Buck et al. | 600/463 |

* cited by examiner

*Primary Examiner*—Brian L. Casier
(74) *Attorney, Agent, or Firm*—Lawrence P. Zale; Mark S. Leonardo (57) ABSTRACT

A motor control apparatus (1) for articulating a probe (3) is constructed with a reversible motor (10) and at least one tension adjusting cable (4) to articulate the probe (3).

36 Claims, 9 Drawing Sheets

NAVIGABLE PROBE AND MOTOR CONTROL APPARATUS

This appln claims the benefit of U.S. Provisional No. 60/024,885 filed Aug. 30, 1996 and Provisional No. 60/051,333 filed Jun. 30, 1997.

FIELD OF THE INVENTION

The invention relates to controls for moving a navigable probe, for example, a medical probe.

BACKGROUND OF THE INVENTION

A navigable probe may comprise, for example, a gastroscope and transesophagel type medical imaging probe as described in U.S. Pat. No. 5,445,154. The probe contains an ultrasound imaging transducer at the end of a flexible cable. The probe is used for medical diagnosis, for example, by inserting the probe inside a body cavity of a patient, and acquiring an ultrasound image by using an ultrasonic transducer. A tip of the probe is adapted to flex to a curved shape in different directions of flexure. Individual torque and articulation control cables extend through the probe. By pulling on individual cables, the probe tip can be flexed or extended to a curved shape, thus, to traverse the probe along bends of a body cavity, and to point the imaging transducer in different directions. The probe cable may contain a torque control cable capable of transmitting a twisting force or twisting motion through the probe and its articulating section while the section is flexed into a curved shape. The torque control cable may be used for transducer rotation to allow imaging along different planes. Adjusting the probe to a curved shape and rotating the torque control cable, currently requires careful hand operation, and hand operation is required to start and stop the movement of the probe to avoid injuring a patient with the robe.

SUMMARY OF THE INVENTION

The invention relates to motorized, controlled movement of a navigable probe actuated by one or more tension adjusting cables. For example, an ultrasound imaging transducer on a tip of a medical imaging probe is articulated by applying tension to the cable.

The invention further relates to a motor control apparatus capable of limiting the force exerted by a navigable probe.

The invention further relates to a motor control apparatus that is capable of limiting the tension applied to one or more articulation control cables, by a limiting system that limits the tension.

The invention further relates to a motor control apparatus that restricts the articulation of a navigable probe to prevent farther articulation of the probe in response to resistance by the surface of that which is being probed, whereby endangering surfaces sensitive to pressure is avoided.

The invention further relates to a motor control apparatus with a slender configuration, which can be operated by one person.

The invention relates further to a motor control apparatus with a slender configuration to hold and manipulate the motor control apparatus with a single hand of a person.

The invention relates further to a motor control apparatus with a slender configuration suitable for mounting in a slender housing.

The invention further relates to a multiposition switch or variable switch of a motor control apparatus to activate reversible motor(s).

The invention further relates to a switch of a motor control apparatus to activate a reversible motor mounted on a housing attached to a probe, to be operated by digits on one hand of a person grasping the housing.

The invention further relates to a medical imaging probe having one or more articulation control cables to flex the probe in variable degrees of flexure of the probe.

The invention further relates to a medical imaging probe wherein an output shaft of a reversible articulation control motor is in-line with a corresponding longitudinal axis of each of one or more articulation control cables, to provide a slender configuration.

The invention further relates to a medical imaging probe wherein, a reversible articulation control motor is parallel to a corresponding longitudinal axis of each of one or morte articulation control cables, to provide a slender configuration.

The invention further relates to a medical imaging probe wherein, a reversible probe articulation control motor has a limited torque output to restrict the articulation of one or more articulation control cables in response to farther movement of the probe being resisted by the surface of that which is being probed.

According to an embodiment, the motor is constructed or governed to provide limited torque output.

According to an embodiment, a reversible motor is provided with a limited torque output to prevent the probe from farther flexure or extension by the reversible motor when such articulation of the probe is resisted.

According to an embodiment, the output shaft of an articulation control motor is parallel with the longitudinal axis of each of one or more articulation control cables, to provide a slender configuration.

According to an embodiment, the output shaft of an articulation control motor is oriented non-parallel to the longitudinal axis of the articulation control cables.

According to an embodiment, one or more multiposition or continuously variable control switches, or rheostats, are provided and are moveable in different directions to actuate reversible torque motors in reversible directions.

According to an embodiment, the control motors are detached from a housing to be activated from a remote location.

According to an embodiment, the articulation control cables are actuated by a gear to gear drive mechanism.

According to an embodiment, the articulation control cables are actuated by a gear to pulley mechanism.

According to an embodiment, the articulation control cables are actuated by a sprocket and chain mechanism.

According to an embodiment, the articulation control cables are actuated by a pulley to pulley drive mechanism.

According to an embodiment, the position of the probe relative to the longitudinal axis of the motor control housing, is indicated by dials mounted on the housing.

BRIEF DESCRIPTION OF THE DRAWINGS

Embodiments of the invention will now be described by way of example with reference to the accompanying drawings, according to which.

DETAILED DESCRIPTION

Figure 1:
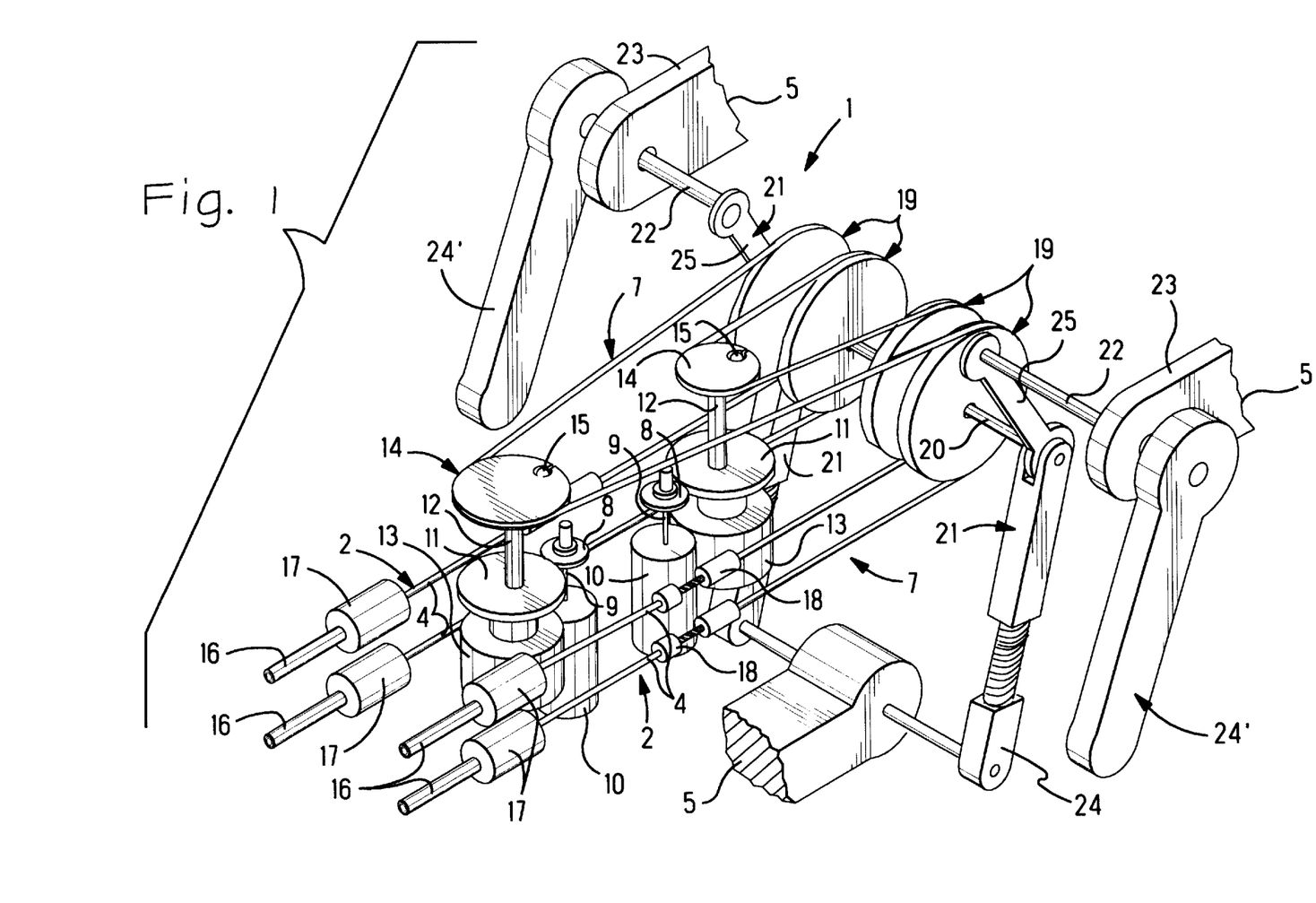
FIG. 1 is a schematic view of a motor control for a medical probe.
Figure 8:
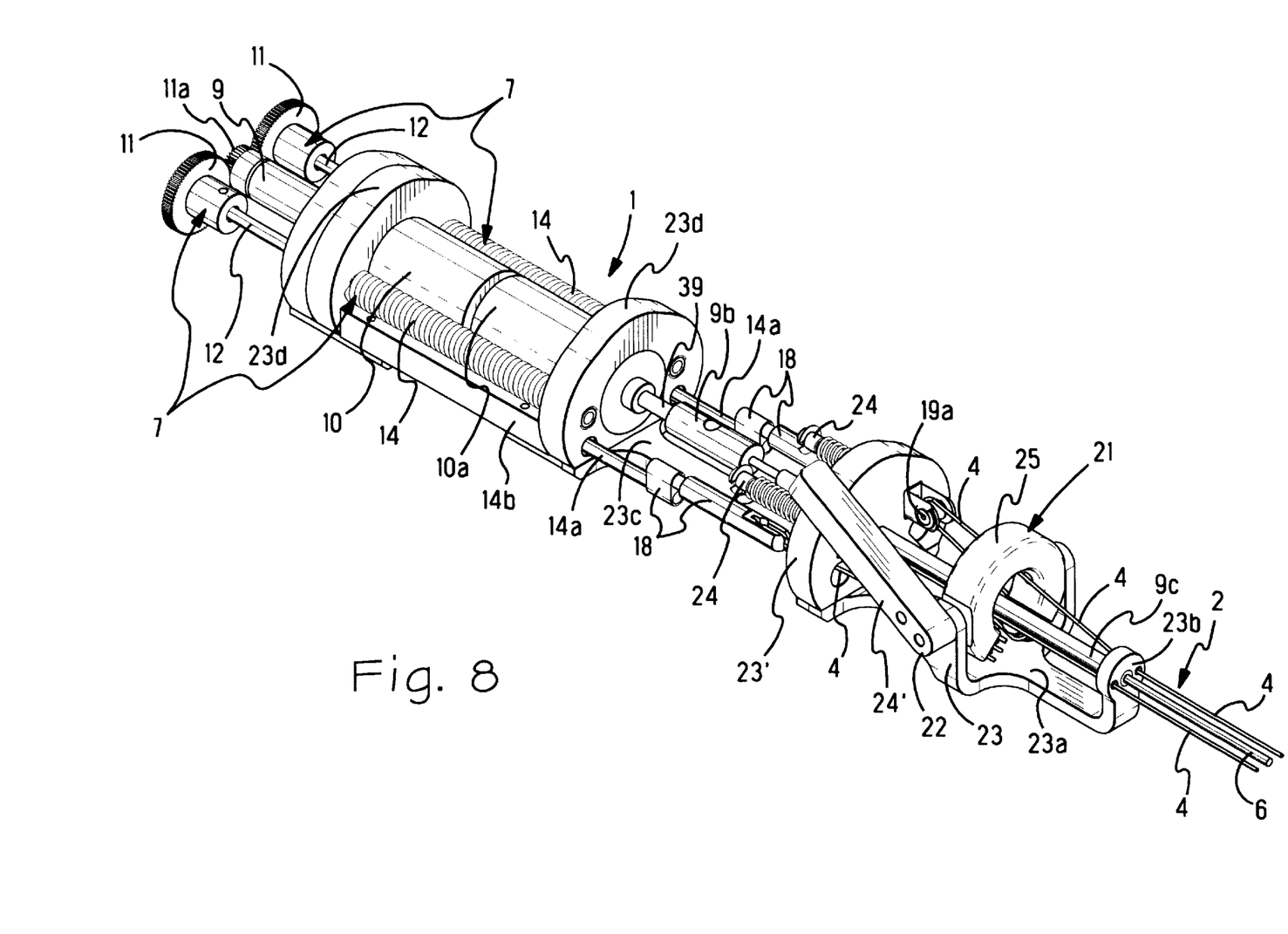
FIG. 8 is an isometric view of an embodiment of a motor control for a medical probe.

With reference to FIGS. 1 and 8, a motor control apparatus (1) for a navigable probe, for example, a medical imaging probe, of an ultrasound imaging transducer, not shown, is comprised of one or more cables (4) extending along a flexible elongated bendable probe (3) to flex the bendable probe (3) to a curved configuration in various degrees of flexure by pulling on one or more articulation control cables (4). As shown in FIG. 1, one articulation control cable (4) is continuous, whereas, in FIG. 8, two articulation control cables (4) may terminate in respective cable ends that comprise a corresponding cable pair (2). According to an embodiment shown in FIG. 1, additional cables (4) may extend along the bendable probe (3) to flex the bendable probe (3) in various degrees of flexure, and in one or more additional directions of flexure, by applying tension to an alternate control cable (4, 4), by alternately pulling on individual cables (4), to effect the articulation of the tip of the probe (3).

Figure 2:
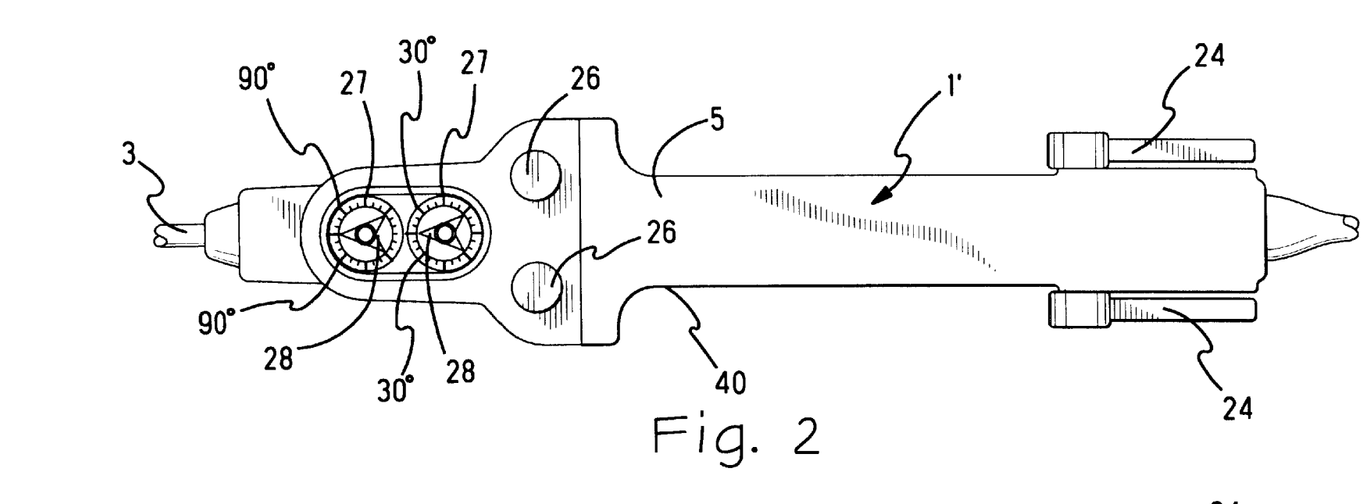
FIG. 2 is a top view of a portion of a medical probe.
Figure 3:
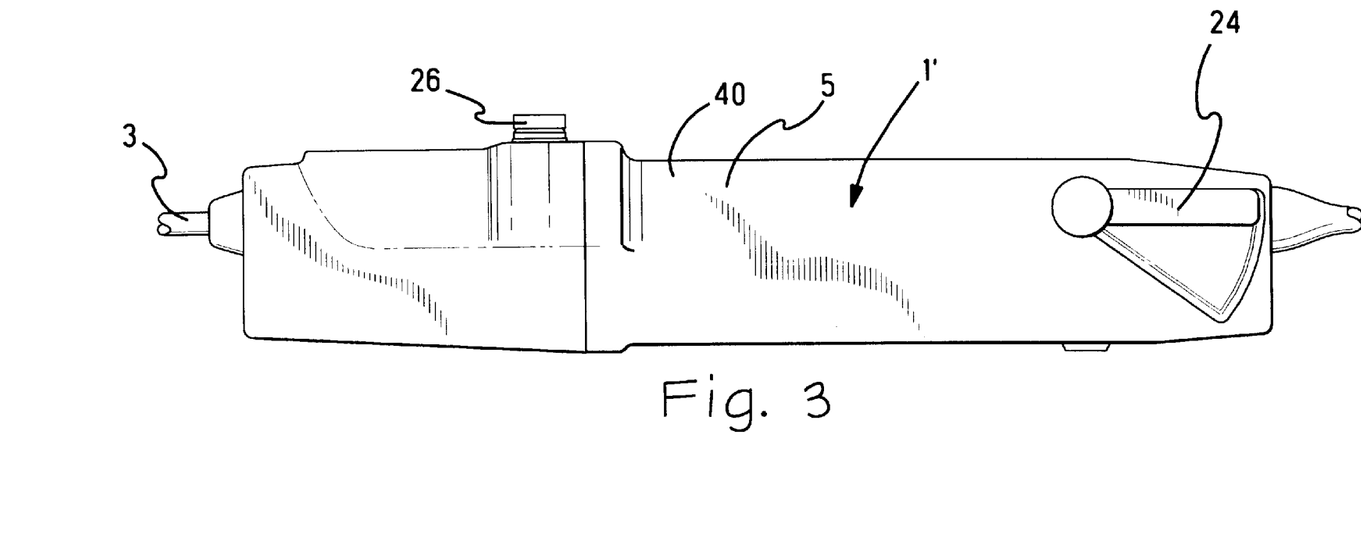
FIG. 3 is a side view of the medical probe portion shown in FIG. 2.
Figure 11:
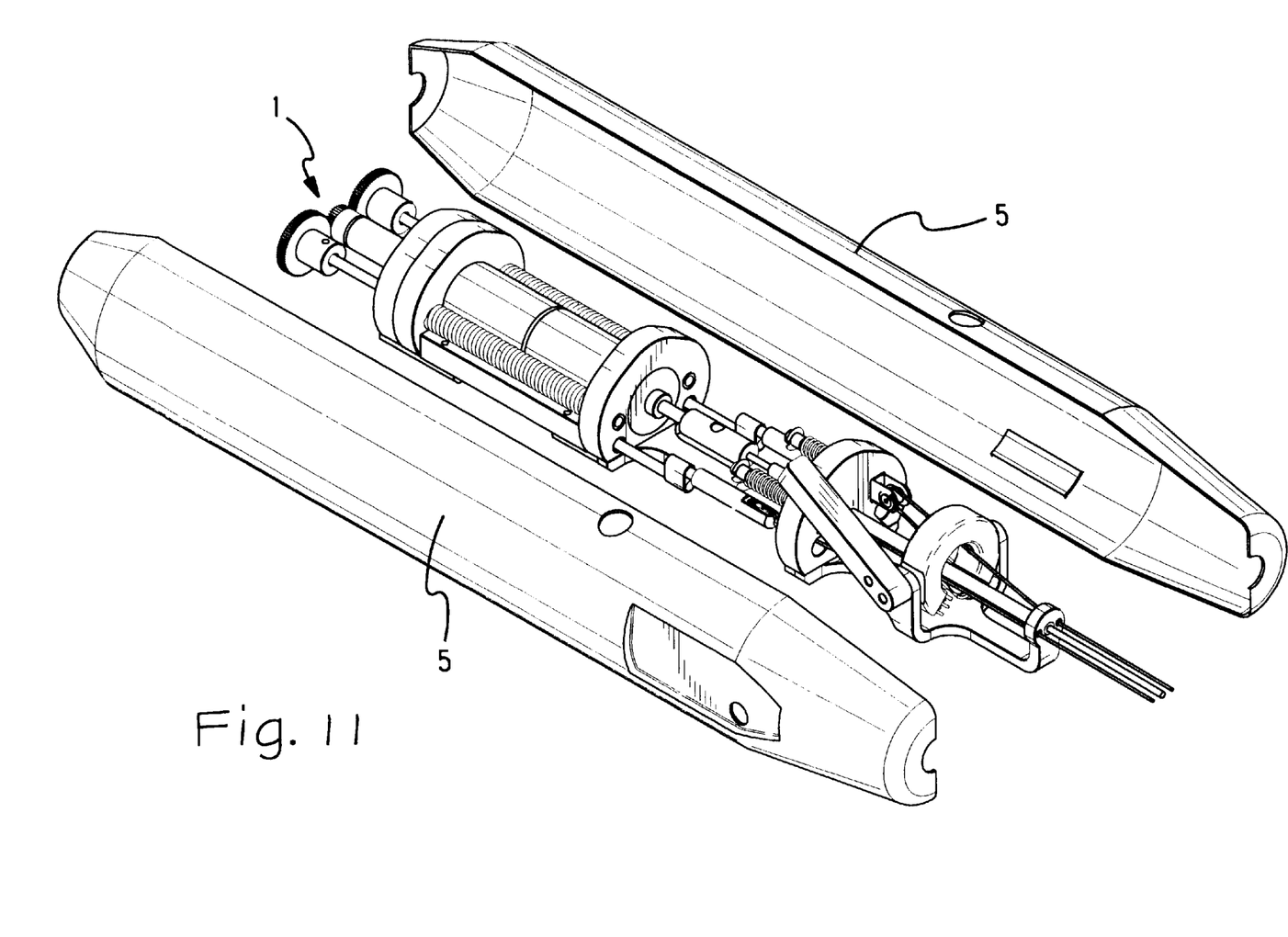
FIG. 11 is an isometric view of the embodiment shown in FIG. 8 for containment in a housing, with housing halves shown separated from one another.

A medical imaging probe is further comprised of the elongated bendable probe (3) attached to a housing (5), FIGS. 2, 3 and 11. Details of the bendable probe (3) are described in U.S. Pat. No. 5,445,154. Individual articulation control cables (4, 4) of each corresponding cable pair (2) are radially spaced from a rotating torque control cable (6), also called, a central control cable (6), FIGS. 4 and 8, extending to a known ultrasound imaging transducer, not shown, on a tip of the articulating end of the probe (3).

By alternately pulling on one or more articulation control cables (4, 4) of the embodiment of FIG. 1, the end of the bendable probe (3) can be flexed in corresponding one or more, for example, four, directions of flexure. In addition, the rotating torque control cable (6) is used to rotate the transducer within the articulating end of the bendable probe (3). By alternately pulling on individual articulation control cables (4, 4) of the corresponding cable pair (2) in each of the embodiments of FIGS. 1 and 8, the bendable probe (3) can be flexed in one direction of flexure forward, then straightened in a backward direction, then curved in a second direction of flexure backward, and therefrom straightened in a direction forward. The motor control apparatus (1), FIGS. 1, 5, 7, 8, 9, 10 and 11, is in an interior of the housing (5) to flex the bendable probe (3), by alternately pulling on individual articulation control cables (4, 4) of the corresponding cable pair (2), imparting individual, reciprocal, or differential movement of the articulation control cables (4, 4). Although two cable pairs (2) are illustrated in FIGS. 1–4, and one cable pair (2) is illustrated in FIGS. 8, 10 and 11, at least one articulation control cable (4) is required to flex the bendable probe (3) to various degrees of flexure. Thus, one or more articulation control cables (4) are intended to be actuated by the motor control apparatus (1).

With reference to FIGS. 1, 2, 3, 7 and 11, the motor control apparatus (1) is mounted on a housing (5), and is adapted to be operated by digits on one hand of a human operator that grasps the housing (5). With reference to FIGS. 8, 9 10 and 11, the motor control apparatus (1) further comprises, a reversible articulation control motor (10) driving a reversible drive mechanism (7) connected to the corresponding articulation control cables (4, 4). A narrow configuration is provided to hold and manipulate the motor control apparatus (1) with a single hand of a person. Referencing FIGS. 8 and 11, for example, the motor control apparatus (1) is parallel with longitudinal axes of the parallel articulation control cables (4, 4). The articulation control motor (10) is in tandem alignment with the axes of the close together, articulation control cables (4, 4). The articulation control motor (10) is a reversible electric torque motor, with its longitudinal axis being parallel with longitudinal axes of the articulation control cables (4, 4), where the articulation control cables (4, 4) extend forwardly of the motor control apparatus (1). A relatively slender dimension of the articulation control motor (10) is oriented transversely of the longitudinal axes of the articulation control cables (4, 4) to result in a slender lengthwise housing (5) that is easily grasped by a human operator.

Further details of an embodiment of the reversible drive mechanism (7) will now be described with reference to FIGS. 1–7. A slip clutch (8) of each reversible drive mechanism (7) connects an output shaft (9) of the articulation control motor (10), for example, a reversible torque motor, to the one or more articulation control cables (4, 4), for the motor (10) to pull on the corresponding articulation control cable (4).

With reference to FIGS. 1–7, the slip clutch (8) is adjusted to slip at a maximum torque output of the articulation control motor (10), as a safety feature, to limit the tension applied to the one or more articulation control cables (4) despite farther rotation of the output shaft (9), in response to flexure of the bendable probe (3) being resisted by a surface of that which is being probed, for example, the surface of organism tissue. With reference to FIGS. 8–11, the articulation control motor (10) is designed to provide a selected, maximum torque output, as a safety feature, to restrict the drive mechanism (7) from farther movement by stopping farther rotation of the output shaft (9) in response to flexure of the probe being resisted. For example, organism tissue can be damaged by increasing the torque output to effect farther movement of the probe (3) to overcome resistance to such movement by the organism tissue. The motor control apparatus (1) is self limiting to restrict farther bending of the articulating portion of the bendable probe (3) when a predetermined, maximum limit to the force on the cable (4) is attained.

Further with reference to FIGS. 1–7, each of the reversible drive mechanisms (7) comprises, the slip clutch (8) engaging a gear (11) on a rotatable shaft (12) of a rheostat potentiometer (13), and being mounted on the shaft (12) with a rotatable pulley (14). Reversible rotation of the output shaft (9) of the articulation control motor (10) will reversibly rotate the shaft (12) of the potentiometer (13) through the slip clutch (8). The corresponding one continuous articulation control cable (4), FIG. 1, is looped around the pulley (14), with at least a portion of one turn. A lock fastener (15), attached to the center of the continuous articulation control cable (4) is threaded through one of the pulley flanges on the pulley (14) to restrain the ends of the continuous articulation control cable (4) from shifting its position relative to the pulley (14).

With reference to FIG. 8, each of the reversible drive mechanisms (7) further comprises, a secondary drive gear (11) coupled to the output shaft (9) of the articulation control motor (10) through another gear (11a) on the output shaft (9). The secondary drive gear (11) is affixed to a rotatable shaft (12) having an external, helical lead screw (14) that actuates a reciprocating shaft (14a). The helical lead screw (14) meshes with a follower in the form of a triangular projection on the shaft (14a). The shaft 14(a) subsequently reciprocates axially through the forward motor mounting block (23d). The shaft 14(a) extends along an open side of a channel (14b) facing the lead screw (14). The lead screw (14) meshes with the reciprocating shaft (14a) through the open side of the channel (14b). Rotation of the lead screw (14) drives the reciprocating shaft (14a) axially, forward and backward, by corresponding reversed rotation of the lead screw (14). With opposite pitch threads, as shown, the lead screws (14) will actuate the reciprocating shafts (14a) in opposite directions. Each reciprocating shaft (14a) is parallel with the parallel longitudinal axes of the articulation control cables (4, 4) to result in a slender housing (5) that is easily grasped by a human operator. The lead screw (14) on one side of the motor (10) has a right hand thread, and the lead screw (14) on the other side of the motor (10) has a left hand thread.

Figure 4:
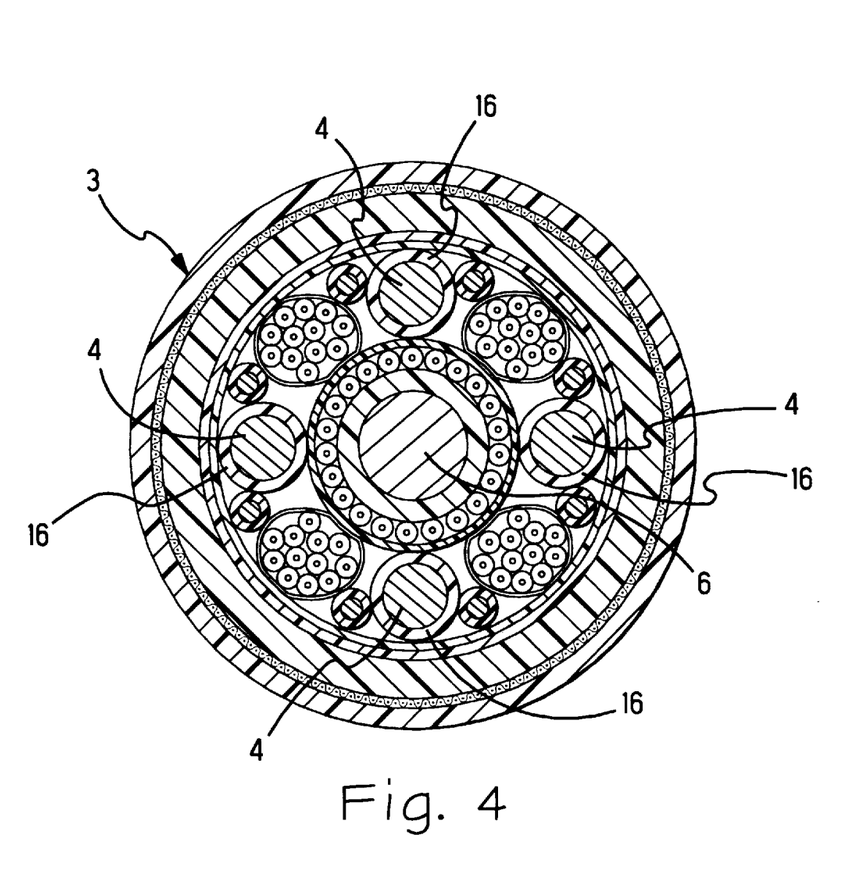
FIG. 4 is a cross section of a flexible probe and its central torque control line and articulation control cables.
Figure 5:
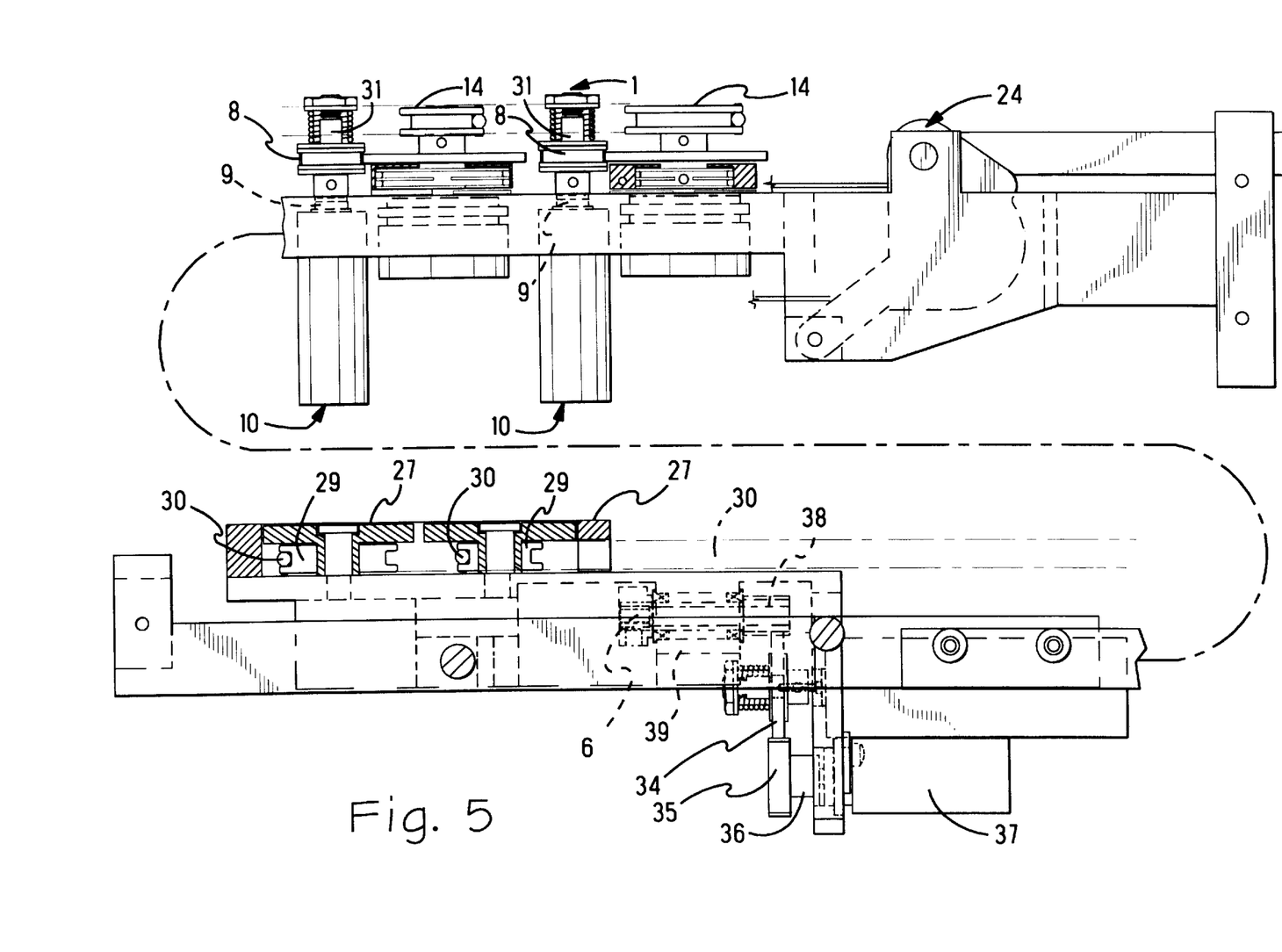
FIG. 5 is a side view of an interior of the medical probe as shown in FIG. 3.

Further with reference to FIGS. 1 and 4, each articulation control cable (4), whether a single continuous articulation control cable (4), FIG. 1, or one of a pair of articulation control cables (4, 4), is enclosed by a sheath (16), FIG. 4, extending along the flexible bendable probe (3). Each corresponding sheath (16) is attached to a sheath holder (17) that concentrically encircles a corresponding control cable (4, FIG. 1. The individual control cable (4) emerges from the sheath holder (17) in FIG. 1.

With reference to FIGS. 1, 8, 9 and 10, the individual control cables (4, 4) connect to respective turnbuckles (18). For example, the turnbuckles (18) are threaded links that adjust the lengths of individual control cables (4, 4). With reference to FIG. 8, respective turnbuckles (18) connect the cables (4, 4) with the reciprocating shafts (14a) through an offsetting link.

With reference to FIG. 1, the individual control cables (4, 4) of the corresponding cable pair (2) extend from respective turnbuckles (18). The control cables (4, 4) extend from opposite sides of the pulley (14) and are turned around the cylindrical peripheries of respective, tension adjusting, toggle pulleys (19). The pulleys (19) are collectively mounted for rotation on a single shaft (20). A spring loaded, toggle link mechanism (21) connects between each opposite end of the shaft (20) and to an axle (22). The axle (22) is rotatably mounted in a bearing block (23) that is attached to the housing (5). With reference to FIG. 8, the bearing block (23) is attached to the housing (5) by being a turned up portion of a rigid frame (23a) that is attached to the housing (5). The frame (23a) provides an eyelet (23b) with respective channels through which the torque control cable (6) extends, and through which at least one articulation control cable (4) extends. The eyelet (23b) gathers the articulation control cables (4) and the torque control cable (6), FIG. 4, closely together in parallel with one another, with their longitudinal axes parallel with the lengthwise, respective motors (10, 10a) to provide a slender configuration. They additionally are in-line with the lengthwise respective motors (10, 10a) to provide a slender configuration. The motors (10, 10a) are mounted to a portion (23c) of the frame (23a) by being secured by motor mounts (23d) that are, in turn, mounted on the portion (23c) of the frame assembly (23a, 23c and 23e).

Each of the toggle links (21) comprises a spring loaded link (24) and a second link (25). An end of the second link (25) is pivotally mounted on the axle (22) rotatably mounted on the bearing block (23). Each end of the axle (22) is secured at the pivoting center of a hand operated, toggle lever (24') mounted on an exterior of the handle (5). Upon rotation of either lever (24') in a clockwise direction, as shown in FIG. 1, each toggle link mechanism (21) comprising the corresponding spring loaded link (24) and a corresponding second link (25) is straightened, causing pivoting of each pulley (19) to apply tension on the corresponding cable pair (2), and couple the corresponding cable pair (2) to the drive mechanism (7). The lever (24') can be pivoted to an off position, for example, by pivoting in a counterclockwise (anticlockwise) direction, causing pivotal motion of each pulley (19) so as to release tension on each corresponding cable pair (2), and to decouple each corresponding cable pair (2) from the drive mechanism (7). With reference to FIG. 8, the respective links (24, 25) are mounted on the frame (23a) in tandem alignment with the respective motors (10, 10a) and respective control line (6) and control cables (4, 4) to provide a slender configuration. The control line (6) and control cables (4, 4) pass through the link 25 that bends in close confinement around the control line (6) and control cables (4, 4), to provide a slender configuration.

Figure 9:
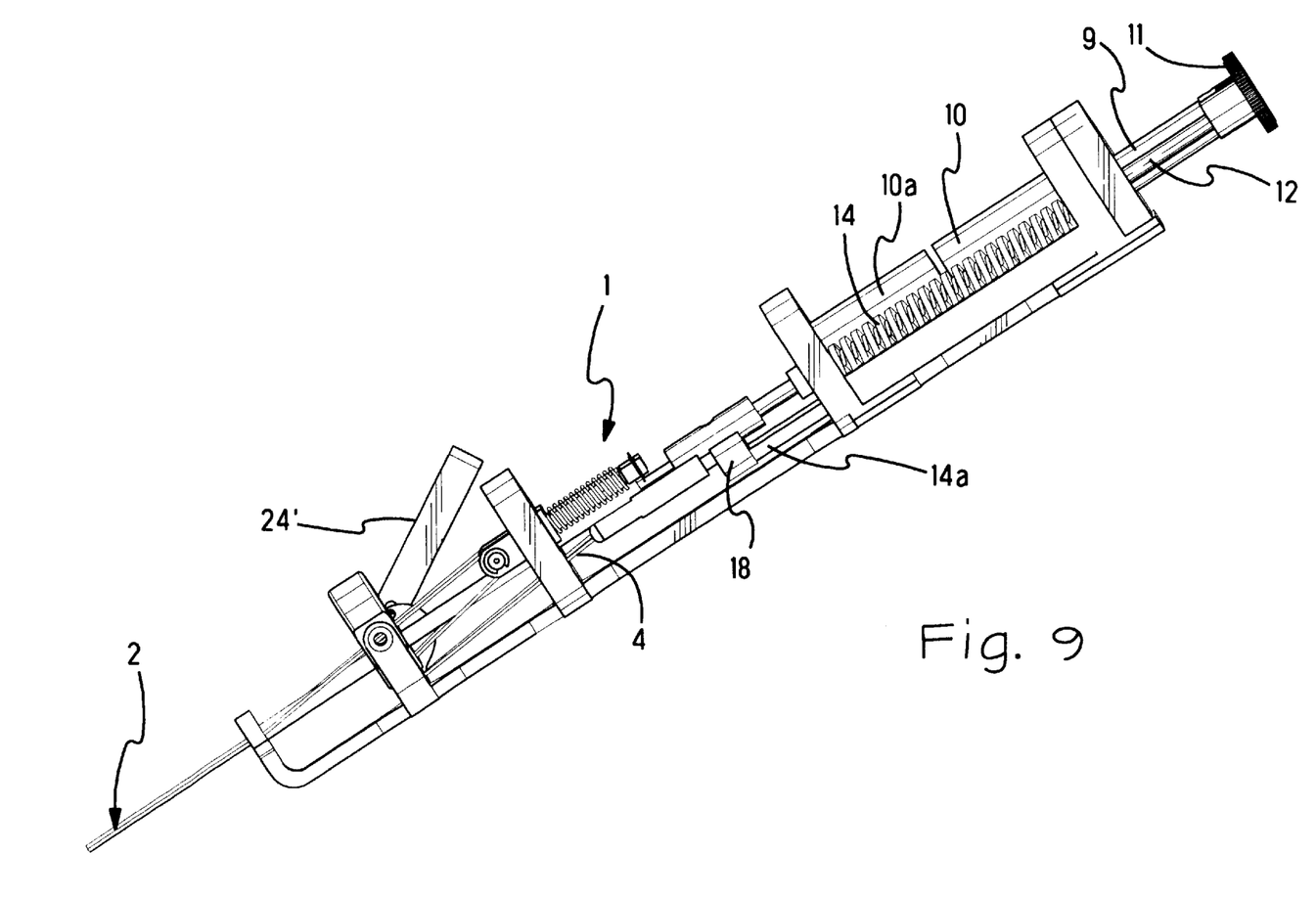
FIG. 9 is a side view of the motor control as shown in FIG. 8.
Figure 10:
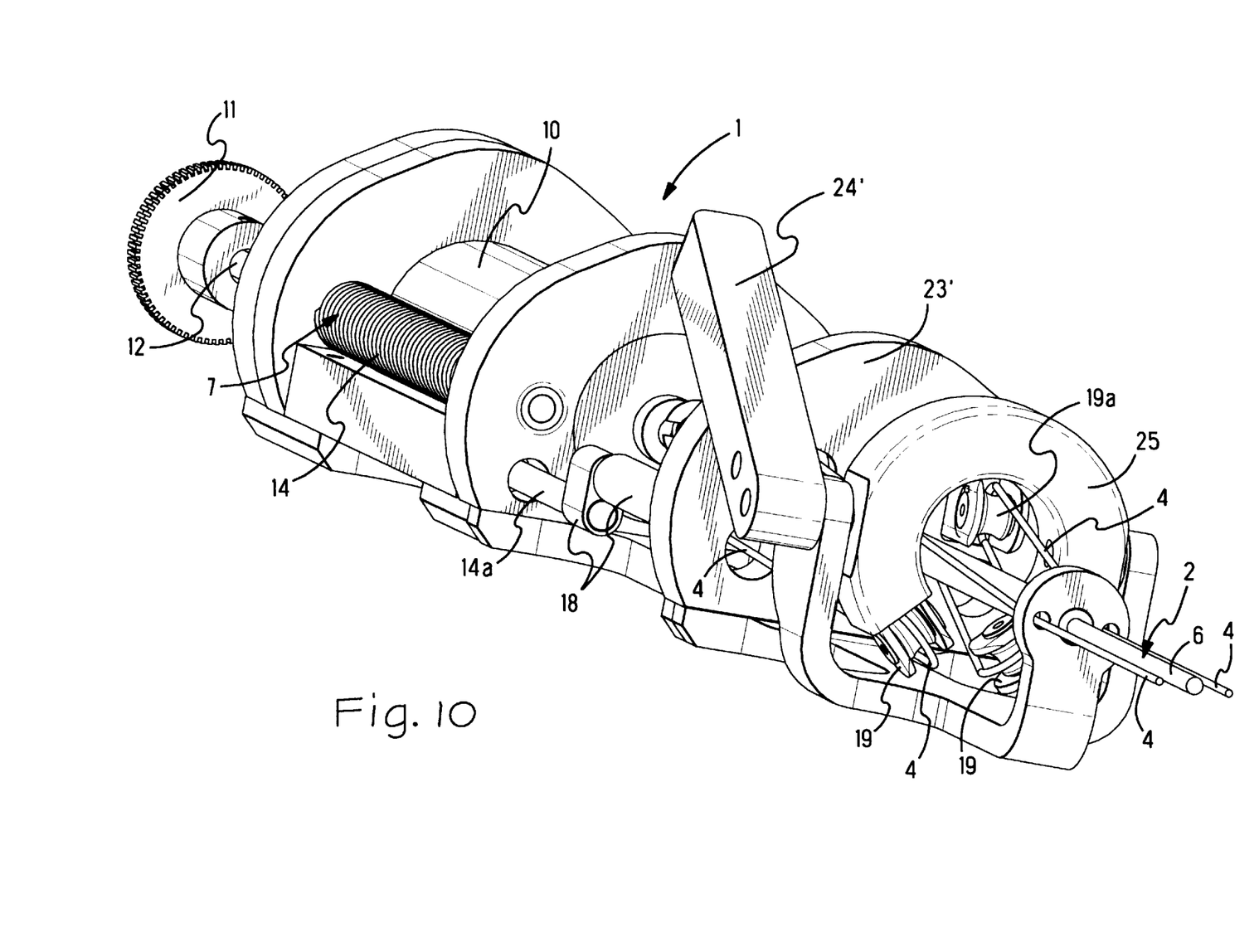
FIG. 10 is another isometric view of the motor control as shown in FIG. 8.

With reference to FIGS. 8–10, the control cables (4, 4) of a corresponding cable pair (2) extend from respective turnbuckles (18), and are turned around the cylindrical peripheries of respective tension adjusting pulleys (19) mounted for rotation on a link (25) of a link mechanism (21). The link (25) is connected by a rotatable shaft (22) to a pivoting lever (24'). The shaft is mounted to a bearing block (23). The control cables (4, 4) extend from the pulleys (19) and are turned around the cylindrical peripheries of respective idler pulleys (19a) that are mounted on spring loaded links (24) of the link mechanism (21). The links (24) extend through a mounting block (23'). The links (24) are spring loaded against the mounting block (23') to bias the pulleys (19a) and apply tension on the control cables (4, 4). The spring loaded links (24) are loaded with nominal spring pressure and apply nominal tension on the control cables (4, 4), preventing over-tensioning of the control lines (4, 4).

The nominal tension of the articulation control cables (4) is maintained by a spring loaded link (24) and a second link (25), for example, comprised of idler shafts (24) attached to pulleys through which the articulation control cables (4,4) are routed. The articulation control cables (4) are also routed through similar pulleys which are affixed in the open ends of a pivotally mounted rotatable yoke of a link mechanism (21). This rotatable yoke is pivotally mounted on an axle (22). The axle (22) comprising this yoke assembly is rotatably mounted on the upturned portion of the mounting plate (23), shown in FIGS. 8, 10 and 11. The end of the axle (22) is secured at a pivoting axis of a hand operated, toggle lever (24') and mounted on an exterior of the housing (5). Upon rotation of the lever (24') in a clockwise direction, as shown in FIGS. 8, 10 and 11, the yoke assembly is moved to a vertical orientation, relative to the baseplates (23a, 23c and 23e), causing pivoting of each pulley (19) to apply tension on the corresponding cable pair (2), and couple the corresponding cable (4), and couple the corresponding cable (4) to the drive mechanism (7). The lever (24') can be pivoted to an off position, for example, by pivoting in a clockwise direction, causing pivotal motion of each pulley (19) so as to release tension on each corresponding cable pair (2), and to decouple each corresponding cable pair (2) from the drive mechanism (7). With reference to FIG. 8, the torque control cable (6) and control cables (4, 4) pass through the central axis of the link 25 that comprises the toggle yoke (25) that bends in close confinement around the cables to provide a slender configuration.

With reference to FIGS. 8–10, the control cables (4, 4) of a corresponding cable pair (2) extend from respective turnbuckles (18), and are turned around the cylindrical peripheries of respective tension adjusting pulleys (19) mounted for rotation on a link (25) of a link mechanism (21). The link (25) may comprise a yoke assembly (25), FIG. 8. The link (25) is connected by a rotatable shaft (22) to a pivoting lever (24'). The shaft (22) is mounted to a bearing block (23). For example, the pulleys (19) are mounted for rotation on the open ends of the rotatable yoke assembly (25). The link (25) is connected by a rotatable shaft (22) to a pivoting lever (24'). The shaft is mounted to a bearing block (23). The control cables (4, 4) extend from the pulleys (19) and are turned around the cylindrical peripheries of respective idler pulleys (19a) that are mounted on spring loaded links (24) of the link mechanism (21). The links (24) extend through a mounting block (23'). The links (24) are spring loaded against the mounting block (23') to bias the pulleys (19a) and apply tension on the control cables (4, 4). The spring loaded links (24) are loaded with nominal spring pressure and apply nominal tension on the control cables (4, 4), preventing over-tensioning of the control lines (4, 4).

With reference to FIG. 10, the lever (24') is pivotable counterclockwise to pivot the link (25), yoke assembly (25), and move the tension adjusting pulleys (19) farther from the pulleys (19a), and to apply tension on the cables (4, 4) to couple the corresponding cable pair (2) to the drive mechanism (1). Tension is relieved in the following manner. Pivoting the lever (24') clockwise moves the pulleys (19) closer to the pulleys (19a), and decouples the corresponding cable pair (2) from the drive mechanism (7).

In operation, any one of the levers (24') of the embodiments shown in FIGS. 1 and 9, can be manually pivoted by a human operator for two purposes. One purpose is to provide a redundant safety feature, or back-up safety feature, to decouple each cable pair (2) from the drive mechanism (7) as a safety feature. The second purpose is to decouple each cable pair (2) from the drive mechanism (7) to prevent accidental movement of the probe, once the articulating end of the bendable probe (3) has been manipulated to achieve a desired curved configuration.

Figure 7:
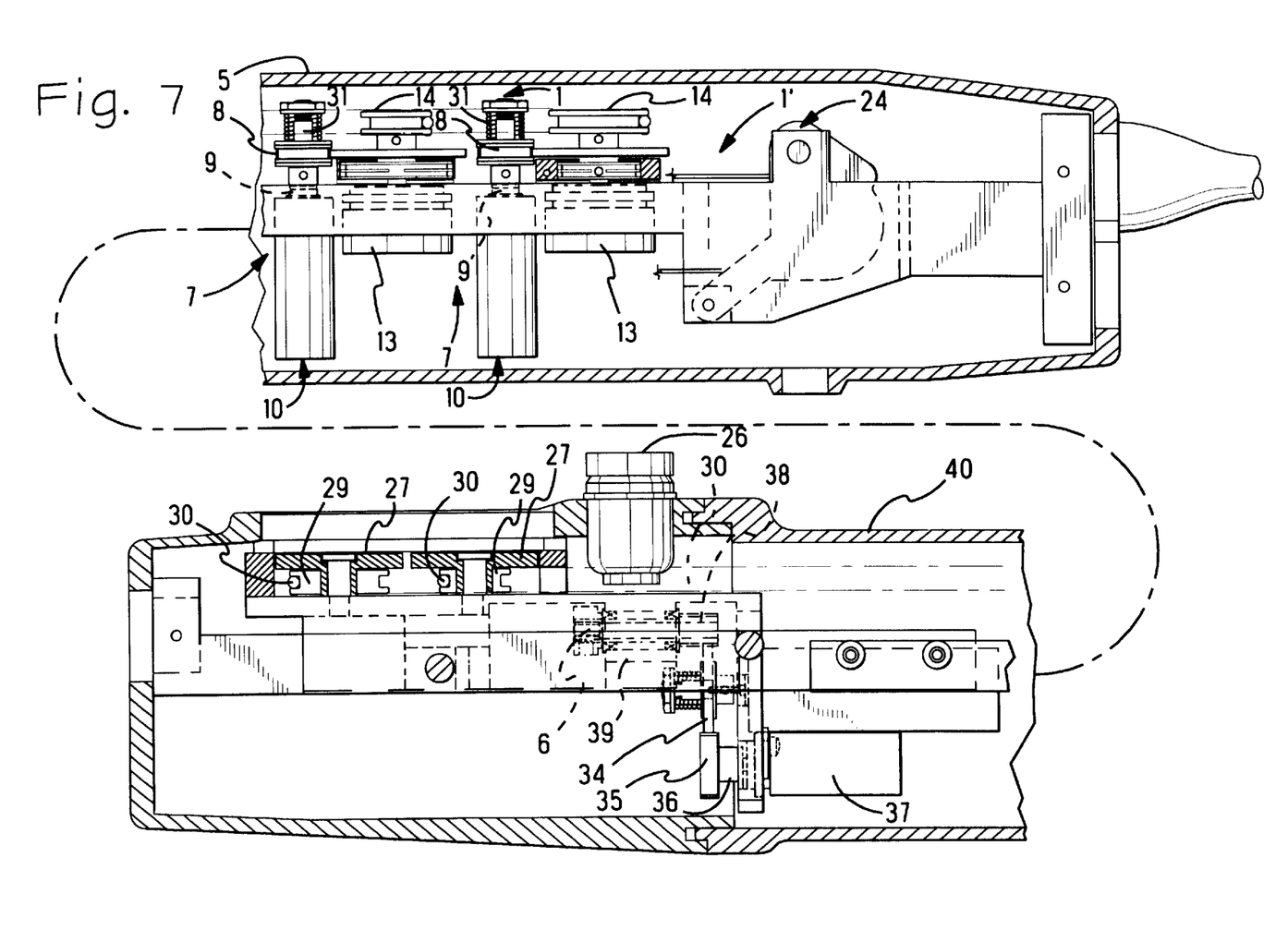
FIG. 7 is a section view of the medical probe as shown in FIG. 3, and further illustrating details of construction.

With reference to FIGS. 2, 3 and 7, mounted on an exterior of each housing (5) is a first multiposition, motor control activation, variable, switch (26), or joy stick, having a top button that is moveable by tilting in four different directions. When the switch (26) is moved by a tilt in one of the directions, the switch (26) completes an electrical connection of a corresponding reversible, torque, articulation control motor (10) to drive the motor (10) in a corresponding direction of rotation. When the switch (26) is moved by a tilt in an opposite direction, the switch (26) completes an electrical connection of the same motor (10) to drive the motor (10) in a reverse direction of rotation. Rotational speed of the motor (10) is controlled, in the embodiment, by tilting the control switch (26) in a different direction.

Figure 6:
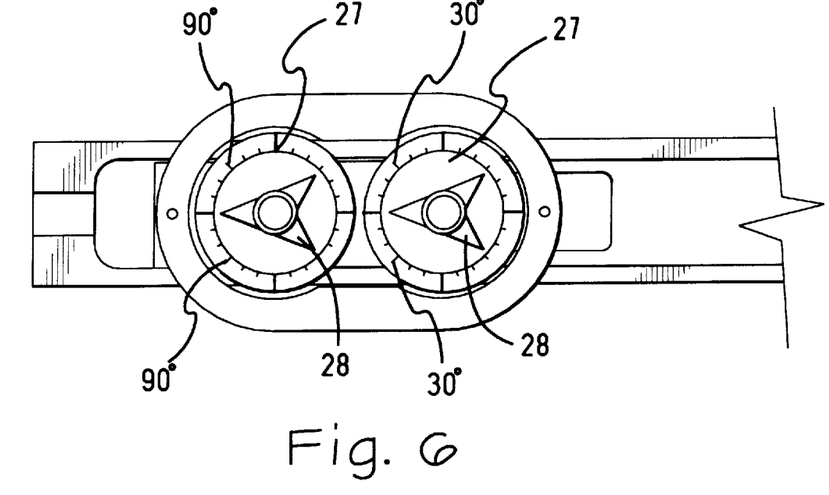
FIG. 6 is a top view of indicator dials indicating pitch and yaw positions of the articulating section of the flexible probe shown in FIG. 4.

In one embodiment, with reference to FIGS. 2 and 6, a first indicator dial (27) is constructed with a mechanically driven needle, to move the needle pointer (28), that is rotated by a timing belt (29) driven by the output rotation of the reversible torque articulation control motor(s) (10). The relative position of the needle pointer (28) on the indicator dial (27) is an indication of the relative curved position of the bendable probe (3) being curved in opposite directions by pulling on alternate control cables (4, 4) of a corresponding cable pair (2). For example, the needle pointer (28) can indicate the vertical pitch relative to a central axis of the uncurved bendable probe (3), and whether the pitch is between (positive) 90° or (negative) 90°. A second needle pointer (28) of a second indicator dial (27) will indicate the horizontal yaw position relative to a central axis of the uncurved bendable probe (3), for example, between positions (positive) 30° left and or (negative) 30° right of an uncurved, central axis of the uncurved bendable probe (3).

With reference to FIG. 8, the control line (6) passes through an elongated hollow tube (9c) and connects to a drive shaft (39) of the torque control cable control motor (10a). The torque control cable (6) connects to the output shaft (9a) of the motor by an adjustable length link (9b).

With reference to FIGS. 2 and 6, a second motor control, or toggle type switch (26) of similar construction to the first switch (26) is mounted on an exterior of the housing (5). The second switch (26) is utilized to rotate the central control, or torque control cable (6), which subsequently rotates the medical imaging transducer at the tip of the articulating end of the bendable probe (3) at the end of the rotatable torque control cable (6). Each indicator dial (27) having a pointer (28) is mounted on a rotatable sprocket (29), FIG. 5. Each sprocket (29) is driven by a corresponding timing belt (30) that loops around a sprocket (31) on a corresponding output shaft (9) of the reversible torque motors (5, 10).

Rotation of the control cable (6) is accomplished by the reversible torque motor (10a), an output shaft of which is connected by a slip clutch (34), FIG. 1, through a gear (35) on a rotatable shaft (36) of a potentiometer (37). The clutch (34) meshes with a gear (38) mounted on a rotatable drive shaft (39). The drive shaft (39) connects to the central torque control cable (6). According to FIG. 8, the drive shaft (39) is the output shaft of the reversible torque motor (10a). The switches (26) are advantageously located adjacent to a grasped section (40) of the housing (5) to be actuated by one of the digits on a hand of a human operator that grasps the section (40). The toggle levers (24) are advantageously adjacent to the section (40) for ease of manual actuation. The one or more switches (26) can be detached from the housing (5), and mounted remotely (not on the housing) and electrically connected to the reversible motors to activate the motors from a remote location.

Known electrical wires, not shown, connect the primary motor (10) and the motor (10a) with a known source of electrical power, such as, a battery or a generator or an electrical outlet, and connect the primary motor (10) and the motor (10a) with respective, known on-off switches or, for example, with the respective switches (26).

Although preferred embodiments have been described, other embodiments and modifications of the invention are intended to be covered by the spirit and scope of the appended claims.

What is claimed is:

1. A medical imaging probe, comprising:
   at least one pair of control cables for bending the probe by equal and opposite simultaneous reciprocating movement of the control cables;

a motor control apparatus connected to the cables;

a reversible motor of the motor control apparatus being coupled to the control cables for imparting equal and opposite simultaneous reciprocating movement of the control cables;

at least one tension adjusting pulley disposed proximately to at least one of said cable pairs and mechanically linked to at least one lever wherein said at least one tension adjusting pulley is moveable by said at least one lever to engage and alternately disengage with the cable pair to couple and de-couple the cable pair from the drive mechanism; and a slip clutch de-coupling the motor from the control cables in response to farther bending of the probe being resisted by organism tissue, whereby damage to the organism tissue is avoided.

2. A motor control apparatus to move a medical probe, comprising:

a primary motor driving a pair of secondary motion transfer mechanisms for transferring power equally to control cables of a corresponding cable pair to effect equal simultaneous reciprocating movement of the control cables to flex the probe to a curved configuration in two alternative directions of flexure; and at least one tension adjusting pulley disposed proximately to at least one of said cable pairs and mechanically linked to at least one lever wherein said at least one tension adjusting pulley is moveable by said at least one lever to engage and alternately disengage with the cable pair to couple and de-couple the cable pair from the drive mechanism.

3. A motor control apparatus as recited in claim 2 wherein, the secondary motion transfer mechanism comprises, a slip clutch connected to the motor, the slip clutch being adjusted to slip in response to movement of the probe being resisted by organism tissue.

4. A motor control apparatus as recited in claim 2 wherein, the motor is provided with a maximum torque output to decouple the drive mechanism from the cable pair in response to flexure of the probe being resisted by organism tissue.

5. A motor control apparatus as recited in claim 2 wherein, the motor is reversible.

6. A motor control apparatus as recited in claim 2 wherein, the motor has its longitudinal axis parallel with longitudinal axes of the control cables to provide a narrow configuration for holding and manipulation.

7. A motor control apparatus as recited in claim 2 wherein, a relatively slender dimension of the motor is transversely of longitudinal axes of the control cables to provide a narrow configuration for holding and manipulation.

8. A motor control apparatus as recited in claim 2 wherein, the motor is a reversible electric motor with its output shaft being parallel with longitudinal axes of the control cables.

9. A motor control apparatus as recited in claim 2 wherein, the secondary motion transfer mechanism comprises, a pair of motor driven lead screws driven by the motor, and the lead screws drive the control cables.

10. A motor control apparatus as recited in claim 2 wherein, the secondary motion transfer mechanism comprises, a reversible drive mechanism.

11. A motor control apparatus as recited in claim 2 wherein, each of the secondary motion transfer mechanism comprises, a gear train connecting the motor with lead screws, and the motor being reversible.

12. A motor control apparatus to move a navigable probe, comprising:

a motor connected to a reversible drive mechanism for pulling on one or more control cables, each of the control cables pulling on the probe to flex the probe in various degrees of flexure; and at least one tension adjusting pulley disposed proximately to at least one of said cable pairs and mechanically linked to at least one lever wherein said at least one tension adjusting pulley is moveable by said at least one lever to engage and alternately disengage with the cable pair to couple and de-couple the cable pair from the drive mechanism.

13. A motor control apparatus to move a navigable probe, comprising:

reciprocating control cables of a cable pair, the cables reciprocating to move the probe to various curved positions;

a primary motor;

a secondary motion transfer mechanism connected between the motor and the control cables to effect equal simultaneous reciprocation of the control cables; and at least one tension adjusting pulley disposed proximately to at least one of said cable pairs and mechanically linked to at least one lever wherein said at least one tension adjusting pulley is moveable by said at least one lever to engage and alternately disengage with the cable pair to couple and de-couple the cable pair from the drive mechanism.

14. A motor control apparatus as recited in claim 13, wherein, the secondary motion transfer mechanism comprises, a reversible drive mechanism, and the motor is reversible to pull on alternate control cables.

15. A motor control apparatus as recited in claim 13, wherein, the motor control apparatus becomes decoupled from the probe when a maximum bending force is attained.

16. A motor control apparatus as recited in claim 13, and further comprising: a slip clutch on an output shaft of the motor, the slip clutch being adjusted to slip upon farther bending of the probe being resisted by organism tissue.

17. A motor control apparatus as recited in claim 13 wherein, the motor is provided with a maximum torque output to decouple the drive mechanism from the cable pair in response to flexure of the probe being resisted by organism tissue.

18. A motor control apparatus as recited in claim 13 wherein, the motor has its longitudinal axis parallel with longitudinal axes of the control cables to provide a narrow configuration for holding and manipulation.

19. A motor control apparatus as recited in claim 13 wherein, a relatively slender dimension of the motor is transversely of longitudinal axes of the control cables to provide a narrow configuration for holding and manipulation.

20. A motor control apparatus as recited in claim 13 wherein, the motor is in tandem alignment with longitudinal axes of the control cables to provide a narrow configuration for holding and manipulation.

21. A motor control apparatus to move a medical probe comprising:

at least a first corresponding cable pair extending along a flexible probe to flex the probe to a curved configuration in two of four directions of flexure by alternately pulling on individual cables of the cable pair;

each corresponding cable pair being connected to a reversible drive mechanism for alternately pulling on individual cables of each cable pair;

the drive mechanism including a slip clutch connecting an output shaft of a corresponding reversible motor to the corresponding cable pair to pull alternately on the individual cables of the corresponding cable pair, the slip clutch being adjusted to decouple the drive mechanism from the output shaft in response to flexure of the probe being resisted by organism tissue, and a joy stick switch movable in four directions, each reversible motor being connected electrically to two alternative directions of motion of the switch, the switch being mounted on a handle on the probe to be operated by digits on one hand grasping the handle; and at least one tension adjusting pulley disposed proximately to at least one of said cable pairs and mechanically linked to at least one lever wherein said at least one tension adjusting pulley is moveable by said at least one lever to engage and alternately disengage with the cable pair to couple and de-couple the cable pair from the drive mechanism.

22. A motor control apparatus as recited in claim 21 wherein, each motor has a maximum output to decouple the drive mechanism from the torque being transmitted by the output shaft in response to flexure of the probe being resisted by organism tissue.

23. A motor control apparatus as recited in claim 21, and further comprising, each cable pair being looped around a pulley, the pulley being rotated on a pivotally mounted axle, and at least one manually actuated lever to pivot the pulley and decouple each corresponding cable pair from the drive mechanism.

24. A motor control apparatus as recited in claim 21, and further comprising:

a second corresponding cable pair extending along the probe to flex the probe in two of the four directions of flexure by alternately pulling on individual cables of the second corresponding cable pair.

25. A medical imaging probe, comprising:

at least one pair of control cables for bending the probe by equal and opposite simultaneous reciprocating movement of the control cables;

a motor control apparatus connected to the cables;

a reversible torque motor of the motor control apparatus being coupled to the control cables for imparting equal and opposite simultaneous reciprocating movement of the control cables;

the motor having a maximum torque output corresponding to farther bending of the probe being resisted by organism tissue, whereby damage to the organism tissue is avoided; and at least one tension adjusting pulley disposed proximately to at least one of said cable pairs and mechanically linked to at least one lever wherein said at least one tension adjusting pulley is moveable by said at least one lever to engage and alternately disengage with the cable pair to couple and de-couple the cable pair from the drive mechanism.

26. Apparatus for controlled movement of a navigable probe, comprising:

reciprocating control cables to move a probe to various curved positions; a reversible drive mechanism for alternately pulling on individual control cables to reciprocate the control cables;

a motor connected to the control cables through the reversible drive mechanism to reciprocate the control cables; and at least one tension adjusting pulley disposed proximately to at least one of said cable pairs and mechanically linked to at least one lever wherein said at least one tension adjusting pulley is moveable by said at least one lever to engage and alternately disengage with the cable pair to couple and de-couple the cable pair from the drive mechanism.

27. Apparatus as recited in claim 26 wherein, the motor comprises, a reversible motor.

28. Apparatus as recited in claim 26 wherein, the reversible drive mechanism comprises, a gear connecting an output shaft of the motor with two additional gears, and each of the additional gears being connected with a corresponding lead screw driving a reciprocating shaft, and each reciprocating shaft being connected to a corresponding one of the control cables.

29. Apparatus as recited in claim 26 wherein, the reversible drive mechanism comprises, a gear train connecting an output shaft of the motor with the control cables.

30. A motor control apparatus to flex a navigable probe comprising:

reciprocating control cables of a corresponding cable pair connected to a flexible medical probe, the cables reciprocating to flex the probe to various curved positions;

a reversible motor;

a drive mechanism connected between a rotatable output shaft of the motor and the control cables, the cables being moved in opposite directions with respect to each other upon rotation of the output shaft in one direction to flex the probe in various degrees of flexure; and at least one tension adjusting pulley disposed proximately to at least one of said cable pairs and mechanically linked to at least one lever wherein said at least one tension adjusting pulley is moveable by said at least one lever to engage and alternately disengage with the cable pair to couple and de-couple the cable pair from the drive mechanism.

31. Apparatus as recited in claim 30 wherein, the secondary motion transfer mechanism comprises, a slip clutch connected to the motor, the slip clutch being adjusted to slip in response to movement of the probe being resisted by organism tissue.

32. Apparatus as recited in claim 30 wherein, the motor is provided with a maximum torque output to decouple the drive mechanism from the cable pair in response to flexure of the probe being resisted by organism tissue.

33. Apparatus as recited in claim 30 wherein, the motor has its longitudinal axis parallel with longitudinal axes of the control cables to provide a narrow configuration for holding and manipulation.

34. Apparatus as recited in claim 30 wherein, the secondary motion transfer mechanism comprises, a pair of motor driven lead screws driven by the motor, and the lead screws drive the control cables.

35. Apparatus as recited in claim 30, and further comprising, each cable pair being looped around a pulley, the pulley being rotated on a pivotally mounted axle, and at least one manually actuated lever to pivot the pulley and decouple each corresponding cable pair from the drive mechanism.

36. Apparatus as recited in claim 30 wherein, the reversible drive mechanism comprises, a gear connecting an output shaft of the motor with two additional gears, and each of the additional gears being connected with a corresponding lead screw driving a reciprocating shaft, and each reciprocating shaft being connected to a corresponding one of the control cables.

* * * * *